United States Patent [19]

Heitzhaus et al.

[11] Patent Number: 5,356,678
[45] Date of Patent: * Oct. 18, 1994

[54] POUCH FOR ABSORBING FLUID

[75] Inventors: Kevin Heitzhaus, Crystal Lake; Lisa Sherman, Palatine; John Hughes, Long Grove, all of Ill.

[73] Assignee: American Colloid Company, Arlington Heights, Ill.

[*] Notice: The portion of the term of this patent subsequent to Mar. 17, 2010 has been disclaimed.

[21] Appl. No.: 26,336

[22] Filed: Mar. 17, 1993

Related U.S. Application Data

[63] Continuation-in-part of Ser. No. 858,206, Mar. 26, 1992, abandoned, which is a continuation-in-part of Ser. No. 785,889, Oct. 30, 1991, abandoned, which is a continuation of Ser. No. 343,812, Apr. 24, 1989, abandoned.

[51] Int. Cl.⁵ .............................. B65D 85/84
[52] U.S. Cl. ...................... 428/35.6; 204/206; 428/34.2; 428/34.3; 428/35.2; 428/35.7; 428/76; 428/200; 428/201; 428/192; 428/474.7
[58] Field of Search ............ 428/34.2, 34.3, 35.2, 428/35.7, 76, 200, 192, 201, 474, 68

[56] References Cited

U.S. PATENT DOCUMENTS

| | | | |
|---|---|---|---|
| 4,124,116 | 11/1978 | McCabe, Jr. | 206/204 |
| 4,186,233 | 1/1980 | Krajewski et al. | 428/213 |
| 4,686,776 | 8/1987 | Matubara | 426/124 |
| 4,699,620 | 10/1987 | Bernardin | 604/385 A |
| 4,748,069 | 5/1988 | Cullen | 428/211 |
| 4,749,600 | 6/1988 | Cullen et al. | 428/76 |
| 4,853,266 | 8/1989 | Cullen | 421/35.7 |

FOREIGN PATENT DOCUMENTS

| | | |
|---|---|---|
| 0395223A2 | 10/1990 | European Pat. Off. |
| 1800221 | 4/1970 | Fed. Rep. of Germany |
| 2234688A | 2/1991 | United Kingdom |

Primary Examiner—Archene Turner
Attorney, Agent, or Firm—Marshall, O'Toole, Gerstein, Murray & Borun

[57] ABSTRACT

A pouch for absorbing liquids. On one embodiment, the ouch is formed from two distinct layers of sheet material—one including thermoplastic fibers for the purpose of heat sealing and the other a tearable tissue paper capable of tearing upon expansion of the water-absorbent material contained between the sheet material layers. In another embodiment, the pouch is manufactured to include a relatively weak sealed seam, e.g., formed by heat sealing adjacent sheet material layers together, that has a weaker bonding strength than one or more other sealed seams, such that upon expansion of the water-absorbent material, the relatively weak seam separates or delaminates into its separate layers to allow the absorbent to spread beyond the pouch at the relative weak seam. In both embodiments, the pouches contain an inner layer of water-insoluble, liquid-absorbing material, such as cross-linked sodium polyacrylate.

34 Claims, 3 Drawing Sheets

POUCH FOR ABSORBING FLUID

CROSS REFERENCE TO RELATED APPLICATIONS

This application is a continuation-in-part of copending application Ser. No. 07/858,206 filed Mar. 26, 1992 now abandoned which is a continuation-in-part of application Ser. No. 07/785,889 filed Oct. 30, 1991, now abandoned, which is a continuation of application Ser. No. 07/343,812 filed Apr. 24, 1989, now abandoned.

FIELD OF THE INVENTION

The present invention relates to a new and improved pouch for absorbing fluids such as water, alkaline and acidic liquids, organic liquids, saline solutions, urine, blood and other body fluids and a wide variety of other types of liquids, particularly aqueous liquids and chemicals. More particularly, the pouch is designed to accompany a wide variety of different types of packages and/or containers used for carrying, holding and transporting various types of fluids so that in the event the containers leak or rupture, any fluid spilling out will be promptly absorbed with minimal damage to the immediate environment.

The pouch in accordance with the present invention is especially designed and adapted for absorbing contaminated body fluids such as urine, blood and other types of liquids used or obtained for analysis in medical treatment.

In addition, the pouch of the present invention finds commercial utility in packaging for meats and other foodstuffs for absorbing liquids and fluids that may be secreted or released from food. The pouch is useful in packaging to insure a neat and clean appearance in a package free from blood stains and the like, which stains are sometimes present in the packages of meats, poultry, fish and other foodstuffs.

BACKGROUND OF THE INVENTION AND PRIOR ART

Over the years a great deal of progress has been achieved in providing new and improved fluid absorbing media in items such as diapers, sanitary napkins, incontinent garments and industrial spill absorbing ropes, pigs, and the like.

The following U.S. patents disclose various types of fluid and liquid absorbing devices. DePhillips, U.S. Pat. No. 2,527,299 discloses a water impermeable sheet material which is capable of passing vapors therethrough. Hoey U.S. Pat. No. 3,901,240 discloses a permeable polymeric liner on an absorbent pad of foam which disintegrates upon flushing in a sewage system. Kemp U.S. Pat. No. 3,953,638 discloses a multi-ply, absorbent, wiping product having a relatively inextensible inner ply that is bonded to highly extensible outer plys. Burkholder Jr. U.S. Pat. No. 3,959,569 discloses a process for preparing water absorbent articles such as bandages and absorbent pads. Hoey U.S. Pat. No. 4,069,366 discloses a permeable polymeric liner for absorbent pad used in sanitary napkins, wound dressings and the like. Holst, et al. U.S. Pat. No. 4,200,558 discloses a process for producing hydrophilic articles from water insoluble polymers. Erickson U.S. Pat. No. 4,293,609 discloses a flexible absorbent laminate made from a crushed film of lightly crosslinked or water soluble hydrophilic polymers. Fowler U.S. Pat. No. 4,372,309 discloses a moisture absorbent pad of wood pulp impregnated with a starch polymer or an acrylic based polymer and useful in absorbing liquid wastes such as urine and the like.

Wahlquist, et al. U.S. Pat. No. 4,379,192 discloses a nonwoven, melt blown, absorbent barrier fabric useful in hospitals, such as surgical drapes and the like. Dehnel U.S. Pat. No. 4,392,908 discloses a process for making water-absorbent articles having water-soluble polymers fixed to a water-absorbent substrate. Dawn, et al. U.S. Pat. No. 4,411,660 discloses an absorbent product for body wastes such as urine and fecal matter employing multiple layers of material for passing and absorbing fluids and liquids, and having a layer for contact with the skin which is leak-proof. Michaels U.S. Pat. No. 4,223,061 discloses an internal body drug dispenser using liquid swellable material to expand and disperse the drug.

Korpman U.S. Pat. No. 4,449,977 discloses a flexible, non-disintegrative, absorbent product having a water-insoluble, non-swelling matrix. Haq, et al. U.S. Pat. No. 4,603,069 discloses a sheet-like article for wiping hard surfaces and the like having an inner layer of liquid absorbing material and bonded together with spot welds between outer sheets. McFarland, et al. U.S. Pat. No. 4,604,313 discloses a fabric-like material containing melt blown material and wood fibers deposited on a foraminous belt. Ness U.S. Pat. No. 4,629,457 discloses an absorbent facing material and method for making the same having a significant one-way valve characteristic for aqueous fluids. Ito, et al. U.S. Pat. No. 4,364,992, discloses a two-layer absorbent article having a super-water-absorbing polymer. Duncan U.S. Pat. No. 4,701,369 discloses an opaque, polymer film laminate having an absorbent surface for absorbing and containing liquids, and Duncan U.S. Pat. No. 4,702,954 discloses an opaque, barrier layer capable of transmitting a vapor therethrough.

McCabe U.S. Pat. No. 4,124,116 discloses a liquid-absorbing enclosure containing absorbent granules surrounded by a filter paper and a dissolvable paper sealed together along the outermost edges. The Cullen, et al. U.S. Pat. No. 4,749,600 teaches water-absorbent pouches containing water-soluble outer covering material.

One aspect of the present invention is to provide a new and improved pouch for absorbing fluids and more particularly to provide a new and improved pouch for absorbing and containing aqueous fluids leaking from packaging, shipping containers and the like during shipment and/or storage.

Another aspect of the present invention is to provide a new and improved pouch of the character described which is especially well adapted for absorbing body fluids, urine, fecal matter, blood and other aqueous body wastes and contaminants in a highly efficient manner to preclude contamination and damage to the immediate environment should liquid leakage occur.

Another aspect of the present invention is to provide a new and improved low cost, highly absorbent pouch of the character described which is resistant to rupture when dry, and is capable of absorbing large quantities of liquid much in excess of the weight and unswollen volume of the pouch itself and easily rupturable, when wetted, to allow the absorbent material to expand beyond the outermost periphery of the pouch.

Still another aspect of the present invention is to provide a new and improved pouch of the character described which will allow for the internal water-absorbing material to break through an outer paper material after absorbing a high volume of liquid.

A further aspect of the present invention is to provide a new and improved pouch of the character described that encapsulates a water-swellable, water-absorbent material, e.g., super-absorbent polymer, between paper or fabric sheet material layers, wherein edges of the pouch are sealed together such that upon expansion of the water-absorbent material, one or more of the seams will separate (delaminate) to permit the material to spread outwardly from the pouch in a desired direction or in a plurality of directions.

Another aspect of the present invention is to provide a new and improved pouch of the character described which is relatively low in cost and yet still capable of absorbing many times its own volume and weight in aqueous liquids.

SUMMARY OF THE INVENTION

The foregoing and other aspects and advantages of the present invention are accomplished in a new and improved pouch for absorbing liquids. In one embodiment, the pouch is formed from two distinct layers of sheet material - one including thermoplastic fibers for the purpose of heat sealing and the other a tearable tissue paper capable of tearing upon expansion of the water-absorbent material contained between the sheet material layers. In another embodiment of the present invention, the pouch is manufactured to include a relatively weak sealed seam, e.g., formed by heat sealing adjacent sheet material layers together, that has a weaker bonding strength than one or more other sealed seams, such that upon expansion of the water-absorbent material, the relatively weak seam separates into its separate layers to allow the absorbent to spread beyond the pouch at the relative weak seam. In both embodiments, the pouches contain an inner layer or volume of water-insoluble, liquid-absorbing material, such as cross-linked sodium polyacrylate, sandwiched between a pair of thin, flexible water-permeable sheet material layers, secured together along at least three of their edges.

In the seam splitting (seam delamination) embodiment, the pouch may be manufactured from a single sheet of material; e.g., tea bag paper, that is folded upon itself, and sealed along three edges to itself, to encapsulate the water-absorbent material in a pouch having only three edges sealed together. In the embodiment that relies upon tearing of one of the sheet material layers, one of the sheet material layers is formed of paper having a relatively low wet tensile strength, particularly in comparison to dry strength, particularly a tissue paper sheet having a wet tensile strength below about 40 grams per 25 mm, preferably below about 30 grams, and more preferably below about 25 grams in the cross-machine direction, as measured by, for example, TAPPI test method T456 OM 87, and most preferably about 10 to about 25 grams, for fast tearing upon becoming wet, and having a dry tensile strength of at least about 200 grams in the cross-machine direction to prevent tearing during manufacture and transport, while dry.

The inner water-absorbent material can be any fibrous, particulate or powdered material that absorbs substantial quantities of water or other liquids, such as lightly to moderately cross-linked sodium polyacrylate, well known for use in diapers, sanitary napkins and incontinence garments.

PAPER TEARING EMBODIMENT

The exterior sheet material secured to the paper sheet material preferably is a woven or non-woven, resilient fibrous or film material having both non-liquid-absorbing thermoplastic fibers as well as liquid-absorbing fibers, such as cellulosic fibers, for drawing the liquid into the interior water-absorbing material from outside the pouch, as known for other purposes, such as packaging desiccants.

The thin flexible, resilient fabric sheet is secured to the paper sheet along adjacent peripheral edges by linear heat seals or by adhesives, such as adhesive strips, to contain the interior liquid-absorbing absorbing material therebetween. The interior liquid-absorbing material may be dispensed or sifted in a thin, substantially uniform thickness layer between the pair of sheet material layers onto an inner surface of the fabric or film sheet held horizontally prior to securing the paper sheet thereto along its edges, or three of the four edges can be secured together and the absorbent material dumped into the three sided pouch from the open side before the fourth side is sealed.

As another example, a pouch is formed by providing an inner layer of liquid-absorbing material, such as a cross-linked polyacrylate, disposed in a thin, substantially uniform layer pressed between the above-described pair of sheet materials and the outer sheets are secured together around peripheral edges after folding over along a fold line initially bisecting the sheet, such that the paper sheet is on the interior.

The pouch can be utilized in packaging foodstuffs of the type having liquids secreted or released therefrom such as meat, fish, poultry, and the like. A liquid-insoluble, liquid-absorbing material is sandwiched between the pair of sheets, the sheets secured along the outer edges, and the sandwich then is placed under the food on a support material or packaged for direct contact with the underside of the food. Any liquid secreted or leached from the food is absorbed in the interior liquid-absorbing material and is normally hidden from view, thus eliminating unappetizing blood stains or other unsightly discolorations and the like from appearing in the package.

SEAM SEPARATION EMBODIMENT

In accordance with another important embodiment of the present invention, the pouch sheet material has sufficiently high wet strength, and at least one of the sheet material seams is sufficiently weak, such that at least one of the pouch seams opens (delaminates or separates) without tearing the pouch sheet material, upon expansion of the swelling water-absorbent material. The expanding water-absorbent material will travel through the open seam(s) beyond the perimeter of the pouch, in the direction of the separated seam(s). For example, a single relatively weak seam can be provided in the pouch to permit expansion of the swelled, water-absorbent material in a desired direction, for example, in a direction where a spill is most likely to spread, e.g., toward a low point of a floor area.

In this embodiment, the paper or other sheet material layers can be formed from any material that will not tear before seam separation, e.g., a paper having relatively high wet strength in the cross-machine direction, e.g., 100–400 grams per 25 mm, as defined with reference to the tearing embodiment. The paper can be coated with a resin film, for heat sealing purposes, or can include thermoplastic fibers, such as the thermoplastic fiber-containing paper material described with reference to the previously described pouch that tears on one side upon expansion of the wetted water-absorbent material.

The weaker heat seal(s) can be accomplished in any manner known in the art. Preferably, the pouch is formed by heat sealing adjacent pouch edges together, using a lower temperature and/or less time and/or less pressure to heat seal the pouch along the seam that will open upon swelling of the contained water absorbent material.

These and other aspects, features, and advantages of the present invention will be apparent to those of ordinary skill in the art in view of the following detailed description of the preferred embodiments, which is made with reference to the drawings, a brief description of which is provided below.

DETAILED DESCRIPTION OF THE PREFERRED EMBODIMENTS

Sheet Tearing Embodiment

Referring now more particularly to the drawings, in FIGS. 1 through 4 there is illustrated a first (sheet material tearing) embodiment of a new and improved pouch for absorbing fluids, referred to generally by the reference numeral 10 and especially adapted and designed to absorb and contain a relatively large volume of liquid 24 coming in contact therewith. The pouch 20 is especially well adapted for the absorption and containment of a wide variety of liquids, particularly aqueous liquids, such as alkaline and acidic liquids, organic liquids, industrial chemicals, water, saline solutions and aqueous body fluids of all types including urine, blood, fecal matter and the like, as well as contaminated medical fluids, particularly urine and blood, which may be shipped in packages and containers, and stored for periods of time.

In the event of spillage and/or leakage of these fluids from packages and containers during storage, handling or transit, it is highly desirable and statutorily mandatory in some cases, that the leaking fluids be absorbed immediately without any spreading of liquid into adjacent containers or cartons, and without contaminating or desanitizing the immediate environment.

The pouch 10 is also especially adapted for containing water and chemical spills, as well as aqueous solutions of acid and alkaline mixtures so that deterioration of the immediate environment where the spills or leakages occur, is minimized or eliminated altogether. Moreover, the pouch 10 is well suited for use in body garments for humans and animals for collecting and containing fluids and aqueous liquids that are secreted and released from the body. In addition, the absorption of these fluids in the pouch 10 is accomplished in a manner that results in a minimal amount of discomfort and in a manner which minimizes the wetness of the collected liquids on the skin or surface of the human or animal involved. The pouch 10 can be especially formulated for protecting the environment against leakages and spills of a wide variety of industrial chemicals, paints, solvents and other fluids and liquids which normally move in commerce and industry and which, if uncontrolled, upon leakage or spillage will cause grave damage and deterioration to the environment.

Figure 1:
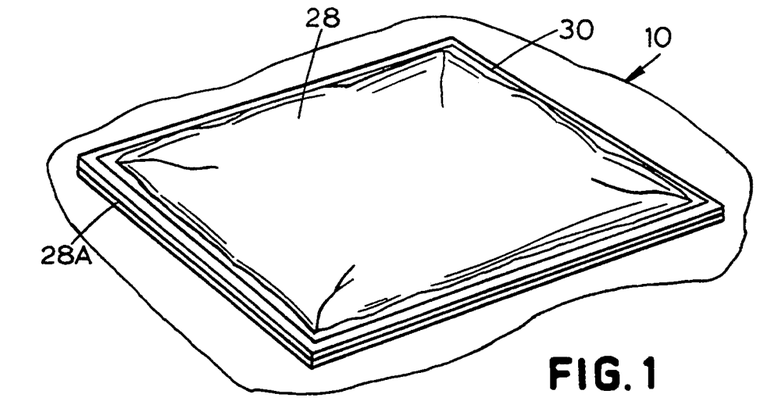
FIG. 1 is a perspective view of a new and improved pouch constructed in accordance with a first (tearing) embodiment of the present invention and shown in a relatively thin, flat condition after tissue sheet rupture after contact with and absorption of liquid.
Figures 2, 3, 4:
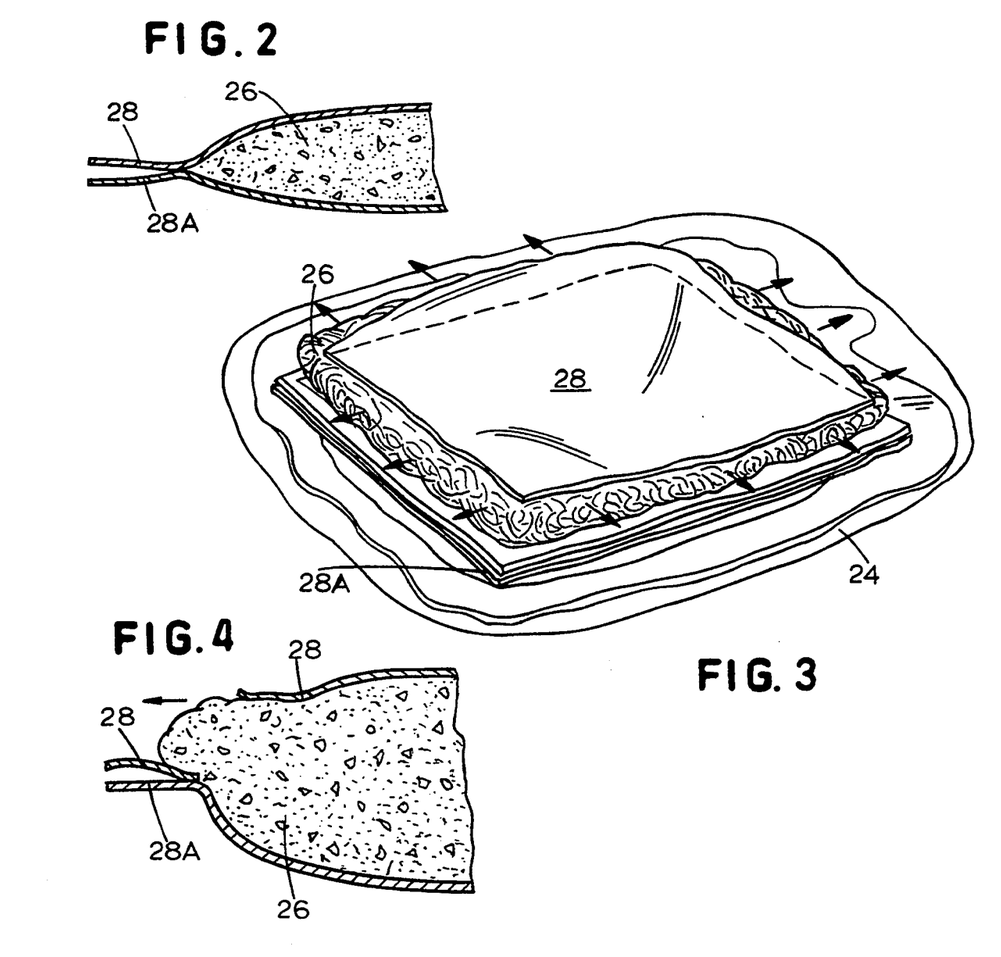
FIG. 2 is a fragmentary transverse cross-sectional view of the pouch of FIG. 1, before liquid absorption.
FIG. 3 is an enlarged, elevational view of the pouch of FIG. 1, shown after the pouch has enlarged in size and weight and the paper sheet material portion 28 split because of the outward forces resulting from absorption of substantial liquid therein.
FIG. 4 is an enlarged, fragmentary transverse cross-sectional view of the pouch of FIG. 1, showing the initial rupture of tissue sheet 28.

Referring now more particularly to FIGS. 1 and 2, the pouch 10 comprises an inner or inside layer of water-insoluble, liquid-absorbing material, e.g., polymer material 26, preferably in powdered or particulate form and preferably contained in a layer, disposed between two sheets of flat, thin, flexible resilient, sheet materials including a tissue paper sheet material layer 28 having a wet tensile strength in the cross-machine direction below about 40 grams, preferably below about 25 grams, TAPPI test method T456 OM 87; and sheet material layer 28A containing both thermoplastic fibers and liquid absorbing, e.g., cellulosic fibers, preferably having a dry tensile strength of at least about 50 grams in the cross-machine direction, and preferably at least about 200 grams in the cross-machine direction and a wet tensile strength in the range of about 200–600 grams (TAPPI test method T456 OM 87). The two sheet material layers 28 and 28A are sealed together along four (4) peripheral edges by means of linear heat seals 30 and/or suitable strips of adhesive material. The preferred wet strength resin in tissue sheet 28 is a polyamide resin, e.g., polyamide epichlorhydrin, capable of heat sealing to sheet material layer 28A. Heat seals are formed by compressing the sheet material halves 28 and 28A tightly under heat and pressure to form heat seals 30, suitable to melt and bond thermoplastic material (film or thermoplastic fibers) from sheet material layer 28A to seal against paper (tissue) layer 28 to provide a permanent line of seal 30.

In the preferred method of manufacturing the pouch 10, a layer of liquid-absorbing material 26, e.g., sodium polyacrylate, in particulate, powdered, or granulated form is sifted onto approximately one-half of a rectangular piece, preferably flexible thermoplastic-containing fabric sheet 28A to a substantially uniform depth except for small strips forming narrow margins around the peripheral edges. The uncovered opposite paper half portion of the sheet 28 is then laid over sheet 28A to lie on top of the thin layer of liquid-absorbing material 26. Heat sealing then is accomplished along four (4) linear heat seal lines 30 by the application of heat and pressure to complete the closure or sealing of the pouch 10 containing the desired weight and thickness of the liquid-absorbing material 26, as illustrated in FIG. 2. The heat seals in this embodiment are strong enough so that the tissue sheet will rupture before the heat seals separate.

Subsequently, when the pouch or packet 10 comes in contact with a liquid spillage or leakage 24, as illustrated in FIG. 3, the liquid is drawn through the permeable outer fabric sheet 28A into the interior of the pouch for direct contact with the granules or particles or powdered liquid-absorbent material 26. The liquid-absorbent material 26 rapidly absorbs the contacted aqueous liquid and expands substantially. If sufficient liquid is in contact with the liquid-absorbent material 26, the material 26 expands sufficiently to tear the paper 28 allowing the liquid-absorbent material 26 to spread beyond the exterior dimensions of the packet 10. Because of the very low wet strength of the tissue paper 28, the paper 28 easily can tear along all four (4) exterior sides in close proximity to the heat or adhesive seals 30 to allow the liquid-absorbent material 26 to expand outwardly from the packet 10 in all directions for rapid absorption and immobilization of liquid before contamination of the immediate environment surrounding the packet 10.

As the liquid is absorbed by the pouch 10, polymer material 26 begins to enlarge and swell in size and forms a fluff or gel-like consistency. This action expands the pouch volume from the interior as shown in FIGS. 3 and 4 as more and more liquid is absorbed. The liquid-absorbing polymer 26 swells and enlarges the volume or space between the sheet halves 28 and 28A to at least double or triple the original space or volume of the thin, flat, dry pouch 10 as shown in FIGS. 1 and 2. When the pouch 10 expands sufficiently to exert enough pressure upon the paper sheet 28, and the paper sheet is wetted by absorption of water from the water-absorbent material 26, the wet strength of the paper 28 is insufficient to withstand the pressure exerted by the expanding water-absorbent material 26 so that the paper sheet 28 tears along a line of greatest pressure-usually adjacent the heat seal lines 30 along any and all edges where water is contacted by the pouch 10. Accordingly, the water-absorbent material can expand in volume rapidly outwardly from the pouch 10 in all directions beyond the outer periphery of the pouch 10 to capture a spill or other environmental liquid contaminant in the immediate area surrounding the pouch 10. This increase in volume of water-absorbent material 26 may run as high as 60 to 80 times the original volume of a pouch 10 designed to absorb body fluids and the like.

Preferably, the pouches 10 are formed to be rectangular in shape, however a wide variety of different sizes and shapes can be made to fit a particular type of package or requirement. For example, a triangular pouch can be designed to occupy a corner of a transport vehicle transport area to assure that any spilled liquid does not leak out of a corner of the transport vehicle. A wide variety of standardized sizes may be provided in order to accommodate standard package sizes or standard sized containers that are commonly used. For example, a prototype pouch 10 having a finished rectangular size of approximately $3\frac{1}{4}" \times 2\frac{1}{4}"$ can rapidly absorb liquid 24 within a period of several seconds after initial contact with the liquid occurs. Preferably, the pouch 10 is disposed with the sheet material 28A against a floor and the paper sheet 28 exposed upwardly to allow for rapid expansion of the water-absorbent material 26 beyond the pouch periphery. Further, the sheet material 28, having better strength, will not tear as easily as the paper sheet 28 so that if no spill occurs, the pouch will not spill water-absorbent material 26 and the in-tact pouch 10 easily can be removed or, possibly, reused.

Upon initial contact with a synthetic urine type of liquid, a very high absorption rate obtains initially and then the rate gradually reduces as time elapses and the absorbing polymer 26 approaches saturation.

The pouch 10 is extremely light in weight and is thin and relatively flat when dry as illustrated in FIGS. 1 and 2, and does not attribute to any appreciable increase in size or weight to a package containing liquids which are to be absorbed should they leak or containers rupture during transit, handling or storage. However, once a leak or rupture in a container does occur and the leaking liquid is absorbed by the liquid-absorbing material 26 within a pouch 10, the pouch swells rapidly in size and because of the low wet strength of the paper sheet 28, the pouch tears easily when wet for absorption of liquid well beyond the outer periphery of the pouch 10.

A wide variety of liquid-absorbing materials, particularly super-absorbent polymers 26 are useful in the pouch 10 and preferably these materials are supplied in powder form, in particulates or in suitably sized granules. If the polymers are in powdered form, to achieve the full advantage of the present invention, the material is sized to pass freely through a 20 mesh screen but be retained on a 200 mesh screen, preferably passing a 20 mesh screen and retained on a 100 mesh screen.

For fluids other than aqueous based liquids or body fluids, super-liquid-absorbing polymers often have a capacity of absorbing approximately 50 to 600 grams of liquid per gram of polymer and these types of absorbents work well with fatty fluids, acidic and alkaline liquids and pharmaceutical chemicals.

In particular, for absorbing fluids from foodstuffs such as cut meats, including lamb, beef, pork, veal, poultry and fish, super-liquid-absorbing polymers 26, again, have the capacity to absorb approximately 50 to 600 times their own weight in such liquids.

The water-insoluble, water-swellable absorbing polymers 26, preferred for the absorbent material in the pouch 10 of the present invention, are not particularly limited in structure, except that the liquid-absorbing polymer material should exhibit minimal solubilization and substantial swelling upon absorption of water. Such liquid-absorbing polymers include substituted and unsubstituted, synthetic and natural polymers. The water-absorbing resins usually are lightly to moderately cross-linked and contain hydrophilic moieties such as carboxyl, sulfonate, sulfate, hydroxy, phosphate and/or amino groups or the like.

The water-absorbing polymers 26 useful in the pouches of the present invention also may include substituted or unsubstituted polymers, copolymers or terpolymers of hydrolysis products of starch-acrylonitrile graft polymers; cross-linked carboxymethylcellulose; cross-linked polyacrylamides; and polymethacrylamides; cross-linked polyacrylates; polyvinyl alcohols; polyacrylonitriles; polyvinylpyrrolidones; sulfonated polystyrene; hydrolyzed polyacrylamides; polyethylene oxide; sulfated hydroxyethyl polyacrylates; sulfated polyvinyl alcohol; sulfated hydroxypropyl methacrylate; polymers derived from methacryloxy ethyl phosphate; polymerized alpha, beta-unsaturated carboxylic acids and their salts; polymerized aromatic or heterocyclic sulfonic acids, such as 2-vinyl-3-bromobenzenesulfonic acid and 2-sulfo-5-allylfurane; polymerized aliphatic sulfonic acids, such as ethylene sulfonic acid; alginates; carrageenan; proteins, such as gelatin, and casein; cross-linked gum arabic; agar; gum ghatti; cross-linked polysaccharide; acrylic or methacrylic acid graft copolymers; starch-acrylic acid graft copolymers; hydrolyzed starch-methyl methacrylate graft copolymers; cross-linked polysaccharide-acrylamide copolymer hydrolyzates, such as cross-linked products of hydrolyzed starch-ethyl acrylate graft copolymer, hydrolyzed starch-methyl methacrylate graft copolymer, hydrolyzed starch-acrylonitrile graft copolymer and hydrolyzed starch-acrylamide graft copolymer; cross-linked alkyl acrylate or methacrylate-vinyl acetate copolymer hydrolyzates, such as cross-linked products of hydrolyzed ethyl methacrylate-vinyl acetate copolymer and hydrolyzed methyl acrylate-vinyl acetate copolymer; cross-linked starch-acrylonitrile-acrylamide-2-methyl-propanesulfonic acid graft copolymer hydrolyzates; cross-linked starch-acrylonitrile-vinyl-sulfonic acid graft copolymer hydrolyzates; polyfumaride; polyvinylbenzyltrimethylammonium chloride; cross-linked polymers of alpha, beta-unsaturated acids containing a plurality of carboxyl groups, such as fumaric acid and itaconic acid; and the like. Suitable polymers are also disclosed in this assignee's U.S. Pat. Nos. 4,618,631; 4,654,393; 4,677,174; and 4,703,067, which patents are hereby incorporated by reference.

The liquid-absorbing polymers useful in the present invention additionally include nonhydrophilic monomers, such as styrene, copolymerized with the hydrophilic monomers, as long as the water-absorption characteristics and swellability of the resulting resin are sufficient to allow the resin to function as a fluid loss control agent. The polymers useful in the present invention can be used alone or in admixture, and can be surface treated by various agents, such as polyquaternary amines, to improve the water-absorption, water-retention, organic liquid-absorbing qualities, and water-swellability properties of the polymer. In addition, absorbent fillers such as cellulose pulp, talc, diatamaceous earth, unsaturated comonomers, vermiculite, cellulosic fluff and partially saponified polyacrylate polymers may be used in amounts of about 0.1 to about 50 percent by weight of the absorbent material 26. Anti-caking or powder flow enhancers can be added to prevent powdered liquid-absorbing polymer from caking or crusting, such as fumed silica and/or magnesium stearate, in an amount of about 0 to about 1% based on the weight of liquid-absorbing polymer.

To achieve the full advantage of the present invention, the absorbent polymer 26 is a cross-linked homopolymer of acrylic acid or methacrylic acid, or their salts; a cross-linked homopolymer of acrylic acid or methacrylic acid or their salts, synthesized in the presence of a styrene-maleic anhydride resin; or cross-linked polymers derived from acrylic acid or methacrylic acid copolymerized with styrene, wherein the polymers can be synthesized from a monomer solution either including a styrene-maleic anhydride resin or lacking a styrene-maleic anhydride resin, used alone or in admixture with cross-linked sodium polyacrylate.

To further improve the water-absorbing capabilities of the water-absorbing polymer, the water-absorbing acrylic acid polymer can be co-polymerized with styrene. The improved water-absorption and water-retention characteristics realized by copolymerizing acrylic acid with styrene is fully disclosed in U.S. Pat. No. 4,677,174 and hereby incorporated by reference. Similarly, the improved water-absorption and water-retention characteristics achieved by polymerizing acrylic acid or methacrylic acid, and optionally, styrene in the presence of a styrene-maleic anhydride resin is disclosed in U.S. Pat. No. 4,820,733 which patent is incorporated herein by reference. The benefits achieved by surface treating the polymers with a polyquaternary amine are disclosed in U.S. Pat. No. 4,755,562, also hereby incorporated by reference.

The flexible, fluid-permeable, nonwoven or woven water-permeable fabric or water-permeable polymeric sheet 28A is chosen from a variety of different materials. One such material is sold by the T. H. Dexter Company of Windsor Locks, Conn. and is characterized as a two faced, light-weight, permeable, heat-sealing fabric comprising a blend of thermoplastic fibers, cellulose pulp and other cellulose fibers. Typical properties of a grade 2488 material sold by this company include a weight of 24.6 grams per square meter and an air-permeability of 460 liters per minute, per hundred square centimeters, at 12.7 millimeters of water vapor pressure. Such material has excellent wet strength and dry strength. When the tensile strengths are measured in grams per 25 millimeters, fabric sheets 28A have a dry strength ranging between 5300 to 1990 grams per 25 millimeters and a wet strength of 525 grams per 25 millimeters. When wetted with aqueous solutions, the grade 258 woven/nonwoven fabric sheets 28A have a pH to 5.2, and the sheet material has been tested in accordance with, and meets the specifications of, the United States Food and Drug Administration, Extraction Tests for Food Packaging Materials in Contact with Aqueous Foodstuffs as set forth in 21 C.F.R. § 176.170. When used to absorb meat juices, therefor, the fabric sheet 28A is disposed in contact with the meat and the paper sheet 28 faces downwardly.

In general, the sheets 28A of fluid-permeable fabric or polymer are thin, light and flexible, and for heat seal applications, contain a percent of thermoplastic fibers. When the thermoplastic fibers are subjected to heat and pressure between pinch rolls, the thermoplastic fibers in the sheet 28A are bonded to the paper sheet 28 along four (4) heat seal lines 30 which border peripheral edges of the pouch 10.

In accordance with another embodiment of the present invention, the fabric sheet 28A also contains other fibers which are fluid or liquid absorptive, such as cellulose fibers, and/or fibrous forms of the super-liquid-absorbing polymers previously described herein. By providing the sheets 28A with non-fluid-absorbing heat sealable thermoplastic fibers, having excellent wet strength characteristics, along with a mixture of about 5-50% by weight liquid-absorbing-fibers, these fabric sheets are capable of directly absorbing liquids from the exterior of the pouch 10 and also rapidly passing most of the liquid inwardly through permeations via the wicking action of the absorbent fibers to be picked up and contained by the fluid-swellable, liquid-absorbing material 26 of the inner layer.

As illustrated in FIGS. 3 and 4, when a liquid 24 is absorbed by contact with the pouch 10, the liquid flows through the outer fabric sheet 28A and is absorbed both by the liquid absorbent fibrous material 28A in the outer fabric sheet material 28A and is absorbed by the liquid-absorbing material 26 initially held between the outside layers 28 and 28A. Upon absorption of liquid, the absorbent material 26 swells greatly in size, as illustrated in FIG. 4. As shown in FIG. 3, when the pouch 10 reaches full wet-stretched capacity (FIG. 4), the paper sheet 28 tears upon further expansion of absorbent material 26 to allow the absorbent material 26 to expand outwardly from the outer periphery of the pouch 10 to immobilize spilled liquid from an area well beyond the location of the pouch 10. Dependent on the amount and type of liquid that is absorbed, the absorbent material 26 in pouches 10 may grow in volumetric size up to 60 to 800, typically 50 to 100 times, and when aqueous solutions or water is absorbed, the ratio of dry volume to wet volume may commonly reach 6 to 800. Liquid is absorbed not only in the inner layer of liquid-absorbing polymer 26, but is also absorbed and contained in the hydrophilic fibrous material that is optionally included in the outer fabric sheet 28A preferably forming one of the outside sheet materials of the pouch 10.

Figure 5:
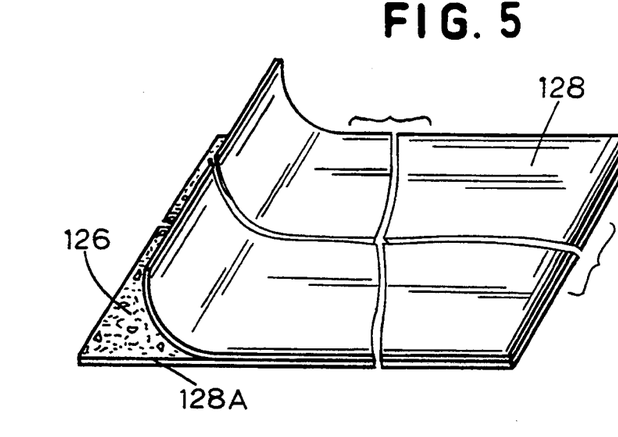
FIG. 5 is a perspective view showing a sheet of liquid absorbing material to be used in a pouch manufactured in accordance with either embodiment of the present invention and shown in a thin, flat condition before any absorption of liquid has taken place.
Figure 6:
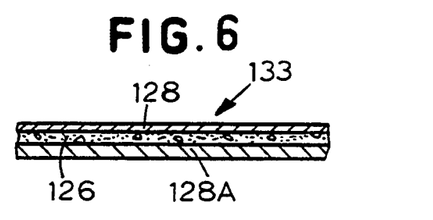
FIG. 6 is a fragmentary, transverse cross-sectional view taken substantially along lines 6—6 of FIG. 5.
Figure 7:
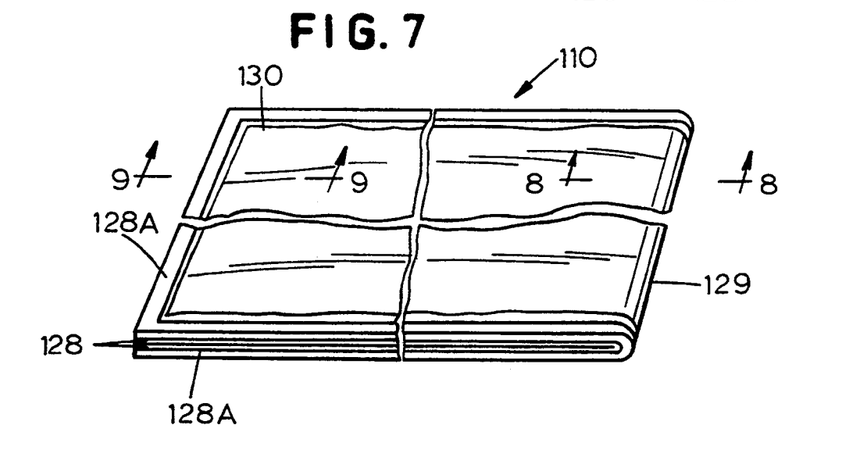
FIG. 7 is a perspective view of the sheet of FIG. 5 after folding in half to provide a modified form of pouch, and shown heat sealed along line 130 using all strong heat seals for the tearing embodiment, or by heat sealing relatively weakly along one or more sides to allow for seam separation (without tearing) for directing swelled water absorbent outwardly from the pouch (in a condition before the absorption of any liquid)
Figures 8, 9:
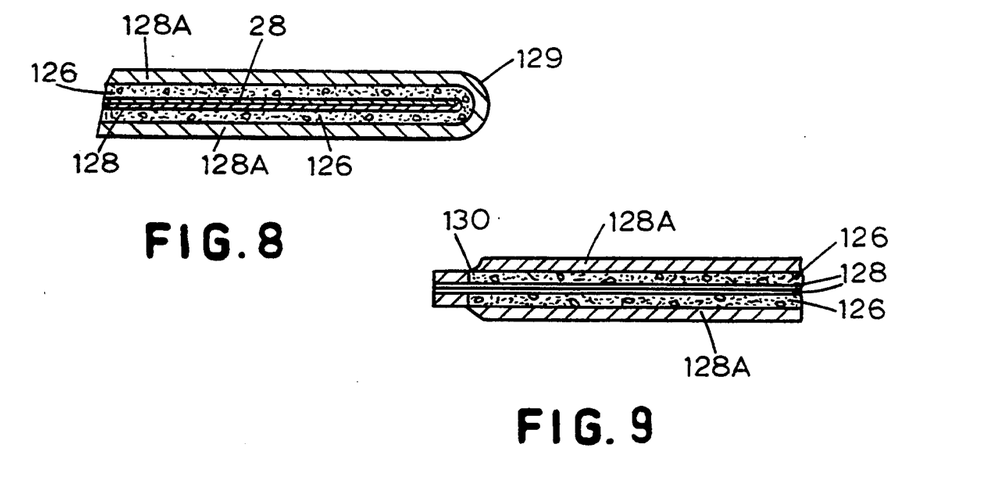
FIG. 8 is a fragmentary, transverse, cross-sectional view taken substantially along lines 8—8 of FIG. 7.
FIG. 9 is a fragmentary, transverse, cross-sectional view taken substantially along lines 9—9 of FIG. 7.

Referring now more particularly to FIGS. 5 through 9, therein is illustrated another example of a pouch constructed in accordance with the features of either embodiment of the present invention and referred to generally by the reference numeral 110 in FIG. 7. The pouch 110 includes an outside layer of fluid-permeable, thin, flexible, woven or nonwoven, resilient, fabric or polymeric sheet 128A which preferably is cut to a rectangular shape, as illustrated. During manufacture of the pouch 110, the lower sheet 128A is positioned directly below a dispensing nozzle or sifter (not shown) which discharges a layer of liquid-absorbing material 126 in granulated, particulate or powdered form to a desired, substantially uniform thickness level, e.g., 1 to 120 mils, on the lower fabric sheets 128A. Thereafter an upper paper sheet 128 having the wet and dry strengths indicated for paper sheet 28 of FIGS. 1-4, or having sufficient wet strength for seam separation instead of sheet tearing, is placed above the layer of liquid-absorbing material 126 and the upper and lower sheet 128 and 128A are then compressed toward one another under suitable pressure to form a unitary, thin, multi-layered, sandwich generally designated 133, as shown in a cross-sectional view in FIG. 6. The same type of sandwich sheet material 133 also may be used in place of the outer fabric sheets 28A or the paper sheets 28 of the previously described pouches, with the paper sheet material 128 facing outwardly. Similarly, liquid-absorbing material 126 may be chosen from the same group of polymer materials 26 as previously set forth herein.

The pouch 110 of FIG. 7 can be formed by folding over a rectangular shaped sheet of sandwich material 133 along a bisecting fold line 129 to form a rectangular or square shape, as illustrated with the woven or non-woven fabric sheet 128A on the upper and lower exterior and the paper sheet 128 on an interior. Liquid absorbed through the outer fabric sheets 128A will be absorbed by the liquid-absorbent material 126 causing the paper to eventually split to permit the absorbent material 126 to expand beyond the peripheral edges of the pouch 110, as in the previous embodiments. Once the fold along one edge 129 is accomplished, three lines of heat sealing 130 are provided along the remaining three open peripheral edges of the rectangular shaped pouch 110, while eliminating the need for a fourth line of heat sealing 130 along the fold line 129 while permitting the pouch 110 to be constructed from both a single relatively strong fabric sheet 128A for seam tearing, or together with an easily wet-tearable paper sheet 128, as previously described.

In accordance with the embodiment of the present invention shown in FIGS. 5 and 6, a sandwich sheet 133 constructed in accordance with FIG. 5 is effectively utilized in the packaging and retail marketing of foodstuffs including meats such as beef, pork, poultry and fish by placing the sheet 133 beneath the foodstuff in an ordinary window package having a covering window of transparent material. In many instances, such foodstuffs tend to secrete or release unsightly liquids such as blood and oil or grease many hours or even days after the initial packaging of the product and these liquids often render the package unappetizing to a potential buyer. By the placement of a sandwich sheet 133 containing liquid-absorbing polymer material 126, disposed so that the fabric sheet 128A faces the foodstuff, under the packaged foodstuff, the liquids secreted from the foodstuff are rapidly absorbed within the liquid absorbing material 126 and discoloration is eliminated or greatly minimized.

Seam Separation Embodiment

In the seam separation embodiment of the present invention, the pouch sheet material has sufficiently high wet strength, and at least one of the sheet material seams is sufficiently weak, such that at least one of the pouch (weak) seams opens or separates (delaminates), without tearing the pouch sheet material, to direct liquid-absorbent material beyond the pouch in the direction of the separated seam(s). A single relatively weak seam can be provided in the pouch to permit expansion of the swelled, water-absorbent material in a desired direction, for example, in a direction where a spill is most likely to spread, e.g., toward a low point of a floor area.

In this embodiment, the paper or other sheet material layers can be formed from any material that will not tear before seam separation, e.g., a paper having relatively high wet strength in the cross-machine direction, e.g., 100-1000 grams, particularly 200-600 grams, as defined with reference to the tearing embodiment. The paper can be coated with a resin film for heat sealing purposes, or can include internal thermoplastic resins during manufacture, or thermoplastic fibers, such as the thermoplastic fiber-containing paper material described with reference to the previously described pouch embodiment that tears upon expansion of the wetted water-absorbent material. Preferably, the pouch is formed by heat sealing adjacent pouch edges together, using a lower temperature and/or less time and/or less pressure to heat seal the pouch along the seam that will open upon swelling of the contained water-absorbent material. Alternatively, a higher temperature can be used to heat seal such that the thermoplastic material partially degrades to provide a weaker seam.

Figure 10:
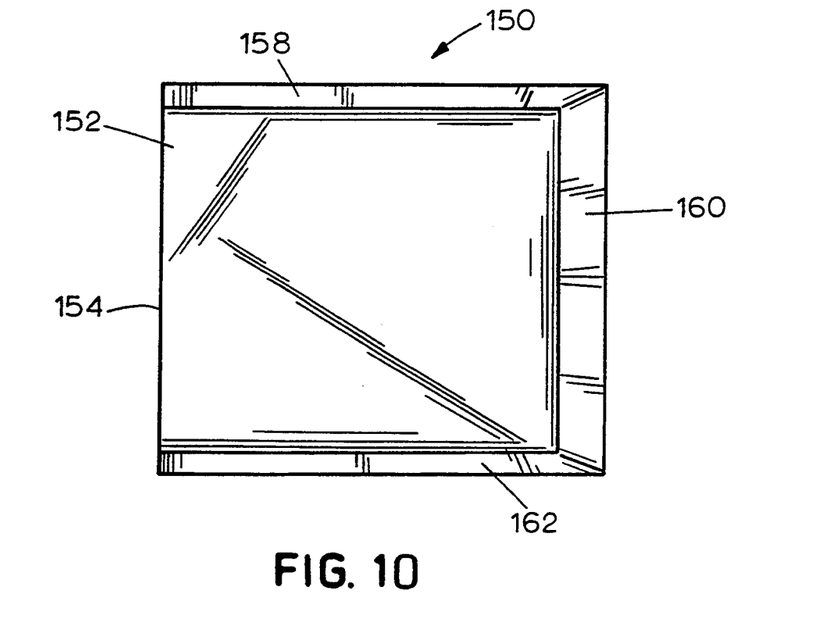
FIG. 10 is a top view of a pouch manufactured in accordance with the second (seam separation) embodiment of the present invention.
Figure 11:
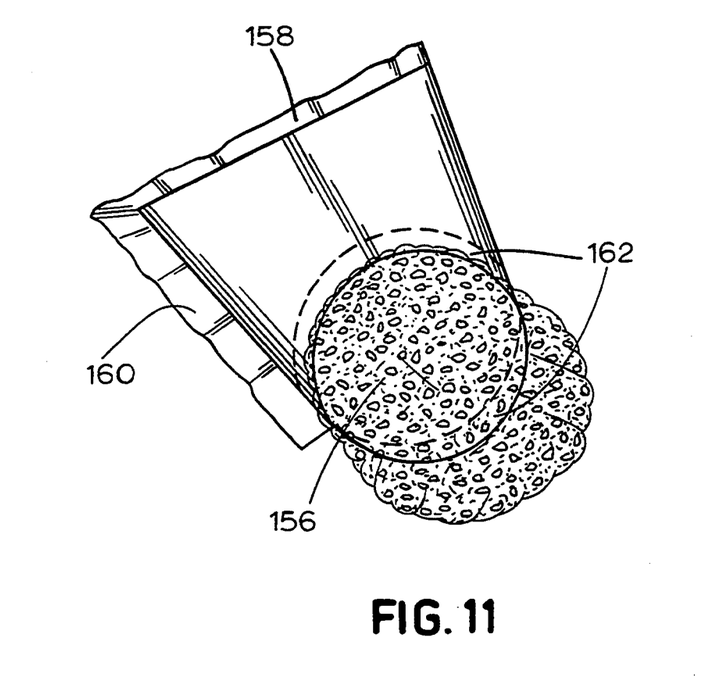
FIG. 11 is a perspective view of the pouch of FIG. 10, showing seam separation (without tearing) after the pouch and absorbent material have enlarged sufficiently for seam separation, at one relatively weak seam, to allow absorbent material expansion beyond the dry pouch periphery.

Referring now to FIGS. 10 and 11, pouch 150, manufactured in a preferred form of the seam separation embodiment of the present invention, is formed from a single sheet of relatively strong, water-permeable paper 152 that is folded over itself at edge 154 to enclose a volume of water-swellable, water-absorbent material, such as cross-linked sodium polyacrylate super absorbent polymer 156. Because of folding a single sheet of paper in half, only three edges require sealing together to prevent escape of super absorbent polymer 156 while the pouch 150 is dry. It should be understood, however, that two separate sheets of sheet material can be used, as described with reference to the first (sheet tearing) embodiment of the present invention, and all four edges of the pouch are then sealed to encapsulate the water-absorbent material.

In accordance with a preferred method of sealing the open edges of the pouch 150 to provide one or more relatively weakly sealed edge(s), for example, two edges 158 and 160 are heat sealed using a higher temperature and/or more pressure, and/or for a longer time than a relatively weakly sealed edge 162, without degrading a hot melt adhesive intermittent coating on the paper 152.

In accordance with this seam separation embodiment, a single sheet material 152 is preferred and can be sealed to itself, e.g., by providing an intermittent coating of a hot melt adhesive, to provide one or more relatively weak heat seal(s) 162, in relation to one or more heat seals 158 and 160 that are stronger than heat seal 162. The preferred sheet material is manufactured by the T. H. Dexter Company of Windsor Locks, Conn. and is characterized as a two faced, light-weight, permeable, heat-sealing fabric comprising a blend of thermoplastic fibers, cellulose pulp and other cellulose fibers. Typical properties of a grade 2588 material sold by this company include a weight of 24.6 grams per square meter and an air-permeability of 460 liters per minute, per hundred square centimeters, at 12.7 millimeters of water vapor pressure. Such material has excellent wet strength and dry strength. When the tensile strengths are measured in grams per 25 millimeters, fabric sheets 152 have a dry strength ranging between 5100 to 1580 grams per 25 millimeters and a wet strength of 500 grams per 25 millimeters. The sheet material has been tested in accordance with, and meets the specifications of, the United States Food and Drug Administration, Extraction Tests for Food Packaging Materials in Contact with Aqueous Foodstuffs as set forth in 21 C.F.R. § 176.170.

Specifications for three suitable outer sheet materials that can be obtained from Dexter (2588, 10DP and 11134) are as follows:

| Comparison of Properties of Grades 2588 and 11134 | | |
|---|---|---|
| | 2588 | 11134 |
| Grammage, g/m² | 24.6 | 24.0 |
| Thickness, microns | 120 | 109 |
| Porosity, 1/min/100 cm² | 460 | 300 |
| Tensile, g/25 mm | | |
| machine direction (MD) | 5100 | 4500 |
| cross-machine direction (CD) | 1580 | 1500 |
| Wet tensile, g/25 mm (CD) | 500 | 500 |
| Boiling delamination, sec. | 150 | 300 |
| Dry delamination, g | 180 | 180 |
| Sifting "B" sand, % loss | 2.3 | 1.0 |
| Infusion: | | |
| 1st color, sec. | 9.8 | 7.5 |

10DP

10DP/C. H. DEXTER provides a breathable substrate which prevents escape of content dust. A non-toxic, hot melt, heat sealable adhesive, coating is applied in a dot pattern to maintain breathability. The adhesive coating has high hot tack and bond strength sufficient to tear package if opening is attempted.

High Porosity

The high porosity of this material facilitates rapid vapor and moisture permeation which increases the effectiveness of absorbent substances contained within the package.

Strong Seals

Adhesive bond strength exceeds the internal strength of the C. H. Dexter material which prevents unintended opening of the package during shipment or by its ultimate recipient.

High Hot Tack Adhesive

Ultimate bond strength is obtained instantaneously after the material is heat sealed which provides superior performance in high speed pouching applications.

Base Substrate

C. H. Dexter, grade 2588

Substrate Basis Weight 15 lbs./3000 sq. ft. or 24.6 grams/sq. meter (nominal)

Coating

10DP adhesive, hot melt, heat seal, clear, dot pattern coating manufactured by Oliver Products Company

Coating Weight 10 lbs./3000 sq. ft. or 16 grams/sq. meter (nominal)

Peel Strength

Exceeds substrate strength, when sealed to itself, approximately 5 lbs./in., or 2300 grams/in. (nominal at a 180 degree peel angle.

GRADE 11134 DATASHEET

Material Description

A two-phase heat seal tissue comprised of a special blend of thermoplastic fibers, manila hemp and other selected cellulose fibers. This tissue has high wet strength combined with neutral odor and flavor characteristics. All materials used to manufacture grade 11134 are certified to be in accordance with 21 CFR 176.10, components of paper and paperboard in contact with aqueous and fatty foods.

| TYPICAL PROPERTIES (NOMINAL VALUES) | | |
| --- | --- | --- |
| GRAMMAGE (BASIS WEIGHT): g/m² DEXTER TM.007 | | 24 |
| HEAT SEAL GRAMMAGE: g/m² DEXTER TM.029 | | 5 |
| TENSILE STRENGTH, DRY: g/25 mm (127 mm GAUGE LENGTH, FLAT JAWS, 423 um/s CROSSHEAD SPEED DEXTER TM.057E DEXTER TM.057F | (MD) (CD) | 4300 1300 |
| AIR PERMEABILITY: L/min/100 cm² @ 12.7 mm WATER DELTA P DEXTER TM.005 | | 400 |
| TENSILE STRENGTH, WET CURED: g/25 mm (127 mm GAUGE LENGTH, FLAT JAWS, 423 um/s CROSSHEAD SPEED) (CURE 600 s @ 176d C) DEXTER TM.059 (SPRAY METHOD) | (CD) | 410 |

In general, the sheet material 152 of fluid-permeable fabric or polymer is thin, light and flexible, and for heat seal applications, contain a percent of thermoplastic fibers. When the thermoplastic fibers are subjected to heat and pressure between pinch rolls, the thermoplastic fibers in the sheet 152 are bonded to itself or another paper or fabric sheet, as disclosed with reference to the tearing embodiment along three (3) or four (4) heat sealed edges, e.g., 158, 160 and 162 which border peripheral open edges of the pouch 160 during manufacture.

In accordance with another embodiment of the present invention, the fabric sheet 152 also can contain other fibers which are fluid or liquid absorptive, such as cellulose fibers, and/or fibrous forms of the super-liquid-absorbing polymers previously described herein. By providing the sheet 152 with non-fluid-absorbing heat sealable thermoplastic fibers, having excellent wet strength characteristics, along with a mixture of about 5-50% by weight liquid-absorbing-fibers, the fabric sheet 152 is capable of directly absorbing liquids from the exterior of the pouch 150 and also rapidly passing most of the liquid inwardly through permeations, via the wicking action of the absorbent fibers, to be picked up and contained by the fluid-swellable, liquid-absorbing material 156 of the inner layer.

As illustrated in FIG. 11, when a liquid is absorbed by contact with the pouch 150, the liquid flows through the outer sheet 152, is absorbed by the liquid absorbent material in the sheet 152 and is absorbed by the liquid-absorbing material 156 initially held between the outside layers of sheet material 152. Upon absorption of liquid, the absorbent material 156 swells greatly in size, as illustrated in FIG. 11. As shown in FIG. 11, when the pouch 150 reaches full wet-strength capacity, the sheet 152 opens at the weak heat seal 162 (without sheet material tearing) upon further expansion of absorbent material 156. The absorbent material 156 then expands outwardly from the outer periphery of the pouch 150 to immobilize spilled liquid from an area well beyond the location of the pouch 150. Depending on the amount and type of liquid that is absorbed, the absorbent material 156 in pouches 150 may grow in volumetric size up to 60 to 800, typically 50 to 100 times, and when aqueous solutions or water is absorbed, the ratio of dry volume to wet volume may commonly reach 6 to 800. Liquid is absorbed not only in the inner layer of liquid-absorbing polymer 156, but also is absorbed and contained in the hydrophilic fibrous material that is included in the outer paper sheet 152 forming one or both of the outside sheet material layers 152 of the pouch 150.

The following Table I illustrates suitable times, temperatures and pressures, useful for forming heat seals 158, 160 and 162:

TABLE I

| TEMP | TIME | PRESSURE (PSIG) |
| --- | --- | --- |
| NON-SEPARATING HEAT SEAL 158, 160 | | |
| 110° C. | 1.2–1.8 SEC | 40–70 |
| 115° C. | 0.8–1.2 SEC | 40–70 |
| 120° C. | 0.5–1.0 SEC | 40–70 |
| 125° C. | 0.4–0.6 SEC | 40–70 |
| SEPARATABLE HEAT SEAL 162 | | |
| 105° C. | 1.0–2.0 SEC | 40 |
| 110° C. | 0.6–1.0 SEC | 40 |
| 115° C. | 0.4–0.5 SEC | 40 |
| 120° C. | 0.3–0.4 SEC | 40 |

Too severe heat sealing conditions also causes weak bonds. Seals that delaminate, therefore, may be created by doubling the acceptable time or by raising the temperature 10°–20° C. at a given time.

The pouch 150 is especially adapted for containing water and chemical spills, as well as aqueous solutions of acid and alkaline mixtures so that deterioration of the immediate environment where the spills or leakages occur, is minimized or eliminated altogether. Moreover, the pouch 150 is well suited for use in body garments for humans and animals for collecting and containing fluids and aqueous liquids that are secreted and released from the body. In addition, the absorption of these fluids in the pouch 150 is accomplished in a manner that results in a minimal amount of discomfort and in a manner which minimizes the wetness of the collected liquids on the skin or surface of the human or animal involved. The pouch 150 can be especially formulated for protecting the environment against leakages and spills of a wide variety of industrial chemicals, paints, solvents and other fluids and liquids which normally move in commerce and industry and which, if uncontrolled, upon leakage or spillage will cause grave damage and deterioration to the environment.

In the preferred method of manufacturing the pouch 150, a layer of liquid-absorbing material 156, e.g., sodium polyacrylate, in particulate, powdered, or granulated form is sifted onto approximately one-half of a rectangular piece, preferably flexible thermoplastic-containing fabric sheet 152 to a substantially uniform depth except for small strips forming narrow margins around the peripheral edges. The uncovered opposite paper half portion of the sheet 152 is then laid over sheet 152 to lie on top of the thin layer of liquid-absorbing material 156. Heat sealing then is accomplished along three (3) linear heat seal lines 158, 160 and 162 by the application of suitable heat and pressure, as illustrated in Table I, to complete the closure or sealing of the pouch 150 containing the desired weight and thickness of the liquid-absorbing material 156, as illustrated in FIG. 2.

Subsequently, when the pouch or packet 150 comes in contact with a liquid spillage or leakage, as illustrated in FIG. 11, the liquid is drawn through the permeable outer sheet material layer 152 into the interior of the pouch for direct contact with the granules or particles or powdered liquid-absorbent material 156. The liquid-absorbent material 156 rapidly absorbs the contacted aqueous liquid and expands substantially. If sufficient liquid is in contact with the liquid-absorbent material 156, the material 156 expands sufficiently to separate the two layers of sheet material 152 along heat seal 162, as illustrated in FIG. 11, allowing the liquid-absorbent material 156 to spread, directionally, beyond the exterior dimensions of the packet 150 in a direction perpendicular to heat seal 162. Because of the relatively high wet strength of the water-permeable sheet material 152, the paper 152 maintains its structural integrity while heat seal 162 separates, allowing the liquid-absorbent material 156 to expand outwardly from the packet 150 for rapid absorption and immobilization of liquid before contamination of the immediate environment surrounding the packet 150.

Preferably, the pouches 150 are formed to be rectangular in shape, however a wide variety of different sizes and shapes can be made to fit a particular type of package or requirement. For example, a triangular pouch can be designed to occupy a corner of a transport vehicle transport area to assure that any spilled liquid does not leak out of a corner of the transport vehicle. A wide variety of standardized sizes may be provided in order to accommodate standard package sizes or standard sized containers that are commonly used. For example, a prototype pouch 150 having a finished rectangular size of approximately 3¼"×2¼" can rapidly absorb liquid 24 within a period of several seconds after initial contact with the liquid occurs. Preferably, the pouch 150 is disposed with the sheet material 152 against a floor and the weak heat seal 162 directed away from the corner to allow for rapid expansion of the water-absorbent material 156 beyond the pouch periphery. Further, the sheet material 152 will not tear during transport and storage, while allowing the wetted water absorbent to expand beyond the dimensions of the pouch 150. If no spill occurs, the pouch 150 will not spill water-absorbent material 156 and the in-tact pouch 150 easily can be removed and reused.

Upon initial contact with a synthetic urine type of liquid, a very high absorption rate obtains initially for pouch 150 and then the rate gradually reduces as time elapses and the absorbing polymer 26 approaches saturation.

The same wide variety of liquid-absorbing materials, particularly super-absorbent polymers 156, are useful in the pouch 150, as described with reference to the tearing embodiment of the present invention.

Although the present invention has been described in terms of several preferred embodiments, it is intended to include those equivalent structures, some of which may be apparent upon reading this description, and others that may be obvious after study and review.

What is claimed and sought to be secured by Letters Patent of the United States is:

1. A pouch for absorbing liquid comprising:
    an outer liquid-permeable, flexible sheet material surrounding a volume of liquid-swellable, liquid-absorbent material, said liquid-absorbing material contained within said outer sheet material in an amount sufficient such that upon absorption of liquid, said liquid-absorbing material swells to a volume that is greater than an inner volume of said pouch, defined by seals along at least three edges of said outer sheet material;
    said outer sheet material including at least one paper sheet material layer having a wet tensile strength below about 40 grams per 25 mm in the cross-machine direction and a dry tensile strength of at least about 200 grams in the cross-machine direction, said sheet material sealed along at least said three edges to define said inner pouch volume to contain said liquid-absorbent material therein; and
    said paper sheet material layer wet strength being such that the swollen liquid-absorbent material will tear the paper sheet material layer to permit the liquid-absorbent material to expand beyond the periphery of the pouch upon absorption of liquid by said liquid-absorbent material.

2. The pouch of claim 1, wherein upon absorption of liquid, said paper sheet material layer ruptures proximate to a sealed edge.

3. The pouch of claim 1, wherein a layer of the outside sheet material includes fibers of resilient thermoplastic, essentially non-absorbing material and fluid-absorbing fibrous material.

4. The pouch of claim 1, wherein said liquid-absorbent material comprises a liquid-absorbing polymer.

5. The pouch of claim 1, wherein said outer sheet material is formed into a pouch by heat sealing adjacent edges of the same, folded over sheet material layers, or by heat sealing two separate sheet material layers adjacent peripheral edges thereof.

6. The pouch of claim 5, wherein said adjacent peripheral edges of said sheet material are secured together with a strip of adhesive material applied between said adjacent peripheral edges.

7. The pouch of claim 1, wherein said intermediate layer comprises a liquid-absorbing polymer in powder from intermixed with fibrous cellulose material.

8. The pouch of claim 1, wherein said liquid-absorbing polymer comprises a water-absorbent, cross-linked polacrylate.

9. The pouch of claim 1, wherein said liquid-absorbing polymer comprises a cross-linked neutralized polyacrylic acid resin.

10. The pouch of claim 1 comprising an inner layer of liquid swellable, liquid-absorbing polymer material sandwiched between (a) a fabric sheet containing both thermoplastic and water-absorbent fibers and (b) a paper sheet having a wet tensile strength in the cross-machine direction below about 25 grams and a dry tensile strength in the cross-machine direction above about 200 grams; said two sheets sealed together along at least three peripheral edges.

11. The pouch of claim 1, wherein:
    said sheet material surrounding said liquid-absorbent materials is folded over along a mid-portion thereof leaving three peripheral edges extending from a fold line; and
    said three peripheral edges of said folded sheet material sheet sealed to itself surrounding said liquid-absorbent material to form said pouch.

12. The pouch of claim 11, wherein said outer sheet material is substantially rectangular in shape and said fold line bisects said rectangular shape.

13. The pouch of claim 12, wherein the two sheets are secured together with lines of non-liquid-absorbing adhesive material along said peripheral edges.

14. The pouch of claim 12, wherein the two sheets are secured together with lines of non-liquid-absorbing adhesive material along said peripheral edges.

15. The pouch of claim 10, wherein a layer of the outer sheet material comprises a two-phase, lightweight, air-permeable, heat seal fabric of blended thermoplastic fibers, and cellulose fibers.

16. The pouch of claim 15, wherein the outer fabric layer of sheet material has a wet tensile strength when completely wetted with water in a range of abut 200–600 grams per 25 mm.

17. The pouch of claim 1 disposed in contact with a foodstuff and the like materials that release liquid therefrom.

18. The pouch of claim 1, wherein a weaker sealed edge is formed by heat sealing said weaker seal using a different temperature, pressure and/or time than other heat sealed edges such that said weaker heat seal will delaminate before the outer sheet material ruptures to allow escape of said liquid-absorbent material through said delaminated heat seal.

19. The pouch of claim 18, wherein said weaker heat seal is formed by heat sealing two adjacent edges of said outer sheet material at a temperature in the range of about 105° C. to about 120° C. and wherein the stronger heat seals are formed at a temperature of about 110° C. to about 125° C., said weaker heat seals formed at a temperature of about 3° C. to about 12° C. below the stronger heat seals.

20. A pouch for absorbing liquid comprising:
an outer liquid-permeable, flexible sheet material surrounding a volume of liquid-swellable, liquid-absorbent material, said liquid-absorbing material contained within said outer sheet material in an amount sufficient such that upon absorption of liquid, said liquid-absorbing material swells to a volume that is greater than an inner volume of said pouch, defined by seals along at least three edges of said outer sheet material;
said outer sheet material sealed along at least said three edges to define said inner pouch volume to contain said liquid-absorbent material therein; and
said sheet material having sufficient wet strength, in relation to a force required to separate at least one of said sealed pouch edges, such that the swollen liquid-absorbent material will expand beyond the periphery of the pouch upon absorption of liquid by said liquid-absorbent material by delamination of one of the sealed edges.

21. The pouch of claim 20, wherein the outside sheet material includes a fabric layer containing fibers of resilient thermoplastic, essentially non-absorbing material and fluid-absorbing fibrous material.

22. The pouch of claim 20, wherein said liquid-absorbent material comprises a liquid-absorbing polymer.

23. The pouch of claim 20, wherein said outer sheet material is formed into a pouch by heat sealing adjacent edges of the same, folded over sheet material layers, or by heat sealing two separate sheet material layers adjacent peripheral edges thereof.

24. The pouch of claim 23, wherein said adjacent peripheral edges of said sheet material are secured together with a strip of adhesive material applied between said adjacent peripheral edges.

25. The pouch of claim 20, wherein said liquid-absorbent material comprises a liquid-absorbing polymer in powder form intermixed with fibrous cellulose material.

26. The pouch of claim 20, wherein said liquid-absorbing polymer comprises a water-absorbent, cross-linked polyacrylate.

27. The pouch of claim 20, wherein said liquid-absorbing polymer comprises a cross-linked neutralized polyacrylic acid resin.

28. The pouch of claim 20, wherein:
said sheet material surrounding said liquid-absorbent material is folded over along a mid-portion thereof leaving three peripheral edges extending from a fold line; and
said three peripheral edges of said folded sheet material sheet is sealed to itself surrounding said liquid-absorbent material to form said pouch.

29. The pouch of claim 28, wherein said outer sheet material is substantially rectangular in shape and said fold line bisects said rectangular shape.

30. The pouch of claim 29, wherein the two sheets are secured together with lines of non-liquid-absorbing adhesive material along said peripheral edges.

31. The pouch of claim 29, wherein the two sheets are secured together with lines of non-liquid-absorbing adhesive material along said peripheral edges.

32. The pouch of claim 20, wherein the outer sheet material comprises a two-phase, lightweight, air-permeable, heat seal fabric layer containing a blend of thermoplastic fibers and cellulose fibers.

33. The pouch of claim 32, wherein the outer sheet material fabric layer has a wet tensile strength when completely wetted with water in a range of about 200–600 grams per 25 mm.

34. The pouch of claim 20, disposed in contact with a foodstuff or the like material that releases liquid therefrom.

* * * * *